US00PP35668P3

(12) United States Plant Patent
Martin

(10) Patent No.: US PP35,668 P3
(45) Date of Patent: Feb. 27, 2024

(54) ***CANNABIS* PLANT NAMED 'ZLT'**

(50) Latin Name: *Cannabis sativa*
Varietal Denomination: ZLT

(71) Applicant: Umami Worldwide, LLC, Las Vegas, NV (US)

(72) Inventor: Chase Martin, Las Vegas, NV (US)

(73) Assignee: UMAMI WORLDWIDE, LLC, Las Vegas, NV (US)

( * ) Notice: Subject to any disclaimer, the term of this patent is extended or adjusted under 35 U.S.C. 154(b) by 0 days.

(21) Appl. No.: 17/950,091

(22) Filed: Sep. 21, 2022

(65) Prior Publication Data

US 2023/0093799 P1 Mar. 23, 2023

Related U.S. Application Data

(60) Provisional application No. 63/247,288, filed on Sep. 22, 2021.

(51) Int. Cl.
*A01H 5/12* (2018.01)
*A01H 6/28* (2018.01)

(52) U.S. Cl.
USPC ..... Plt./258

(58) Field of Classification Search
USPC ..... Plt./258
See application file for complete search history.

(56) References Cited

U.S. PATENT DOCUMENTS

PP33,391 P2 * 8/2021 Schlup ..... Plt./258

* cited by examiner

*Primary Examiner* — Susan McCormick Ewoldt
(74) *Attorney, Agent, or Firm* — Leonard R. Svensson; Intelink Law Group, P.C.

(57) ABSTRACT

The *Cannabis* cultivar 'ZLT' can be briefly characterized by towering green, white and purple streaking resin-coated flowers. With very short internodal space and vigorous growth characteristics, this cultivar is able to produce very high yields for both flower and hash production. 'ZLT' yields as much as 6% from fresh frozen material. Flower clusters have been observed at over 1-1.5' of uninterrupted colas. The unique terpene and flavor profile described, sets this cultivar apart from others currently available.

5 Drawing Sheets

Latin name of the genus and species: *Cannabis sativa.*
Variety denomination: 'ZLT'.

BACKGROUND OF THE INVENTION

The present invention relates to a new and distinct *Cannabis* cultivar designated 'ZLT'. This new cultivar is the result of controlled-crosses between proprietary cultivars made by the inventors. ZLT was asexually produced in Orange, CA via stem cuttings and cloning method by the inventor. Asexual clones have been grown and tested indoors and in greenhouses and the properties are found to be transmissible by such asexual reproduction. The cultivar and its traits are stable through many generations of asexual propagation.

TAXONOMY AND NOMENCLATURE

*Cannabis*, more commonly known as marijuana, is a genus of flowering plants that includes at least three species, *Cannabis sativa, Cannabis indica,* and *Cannabis ruderalis* as determined by plant phenotypes and secondary metabolite profiles. In practice however, *Cannabis* nomenclature is often used incorrectly or interchangeably. *Cannabis* literature can be found referring to all *Cannabis* varieties as "*sativas*" or all cannabinoid producing plants as "*indicas*". Indeed, the promiscuous crosses of indoor *Cannabis* breeding programs have made it difficult to distinguish varieties, with most *Cannabis* being sold in the United States having features of both *sativa* and *indica* species.

Human cultivation history of *Cannabis* dates back 8000 years (Schultes, R E., 1970, Random thoughts and queries on the botany of *Cannabis*. Pages 11-38 in: C R B Joyce, and S H Curry eds., THE BOTAN Y AND CHEMISTRY OF *CANNABIS*. J. & A. Churchill. London, England). Hemp cloth recovered in Europe dates back 6000 years (Small, E, Beckstead, H D, and Chan, A, 1975, The evolution of cannabinoid phenotypes in *Cannabis*, ECONOMIC BOTANY 29(3):219-232). The written record of the pharmacologic properties of *Cannabis* goes back more than 4000 years (Ti, H. 2737 BC. NEI JING SU WEN HUANG TI, Yellow Emperor's Classic on Internal Medicine; referred to without citation in Small et al. 1975 Supra).

The taxonomy and nomenclature of the highly variable genus *Cannabis* (Emboden, W A, 1974, ECONOMIC BOTANY 28(3):304-310; Small, E and Cronquist, A, 1976, TAXON 25(4):405-435; Small E and Cronquist, A, 1977, TAXON 26(1):110; Hillig, K W and Mahlberg, P G, 2004, American Journal of Botany 91(6):966-975), remains in question. This is in spite of the fact that its formal scientific name, *Cannabis sativa* L., assigned by Carolus Linneaus (Linnaeus, C, 1753, SPECIES PLANTARUM, 2:1027, Salvius, Stockholm, Facsimile edition, 1957-1959, Ray Society, London, U.K.), is one of the oldest established names in botanical history and is still accepted to this day. Another species in the genus, *Cannabis indicia* Lam. was formally named somewhat later (de Lamarck, J B, 1785, ENCYCLO- PEDIE METHODIQUE DE BOTANIQUE, 1(2):694-695), but is still very old in botanical history. In 1785, Jean-Baptiste Lamarck published a description of a second species of *Cannabis*, which he named *Cannabis indicia*. Lamarck based his description of the newly named species on plant specimens collected in India. *C. indicia* was described as relatively short, conical, and densely branched, whereas *C. sativa* was described as tall and laxly branched (Schultes R. E. et al, 1974, Harvard University Botanical Museum Leaflets, 23:337-367). *C. indicia* plants were also described as having short, broad leaflets whereas those of *C. sativa* were characterized as relatively long and narrow (Anderson L. C., 1980, Harvard University Botanical Museum Leaflets, 28:61-69). *C. indicia* plants conforming to Schultes' and Anderson's descriptions may have originated from the Hindu Kush mountain range. Because of the often harsh and variable (extremely cold winters, and warm summers) climate of those parts, *C. indicia* is well-suited for cultivation in temperate climates.

Three other species names were proposed in the 1800s to distinguish plants with presumably different characteristics (*C. macrosperma* Stokes, *C. chinensis* Delile, *C. gigantean* Vilmorin), none of which are accepted today, although the epithet "*indica*" lives on as a subspecies of *C. sativa* (*C. sativa* ssp. *indica* Lam., Small and Cronquist 1976 Supra).

In the 20th century, two new names were added to the 50 liturgy of proposed *Cannabis* species: *C. ruderalis* Janis—chevsky and a hybrid, x *C. intersita* Sojak. (Small, E, Jui, P Y, and Lefkovitch, L P, 1976, SYSTEMATIC BOTANY 1(1):67-84; Small and Cronquist 1976 Supra). Further, numerous names have been proposed for horticultural variants of *Cannabis* but as of 1976, "very few of these have been validly published as formal taxa under the International Code of Botanical Nomenclature" (Small and Cronquist 1976 Supra). Moreover, other recent work continues to focus on higher-order evolutionary relationships of the genus. *Cannabis* has been variously ascribed as belonging to mulberry family (Moraceae) (Engler, H G A, Ulmaceae, Moraceae and Urticaceae, pages 59-118 in: A. Engler and K. Prantl eds., 1889, DIE NATURLICHEN PFLANZENFAMILIEN 3(1). W. Engelmann, Leipzig, Germany; Judd, W S, Sanders, R W, and Donoghue, M J, 1994, HARVARD PAPERS IN BOTANY 5:1-51; Humphries, C J and Black—more, S, A review of the classification of the Moraceae, pages 267-277 In: Crane and Blackmore 1989 id.); nettle family (Urticaceae) (Berg, C C, Systematics and phylogeny of the Urticales, pages 193-220, in: P. R. Crane and S. Blackmore eds., 1989, EVOLUTION, SYSTEMATIC, AND FOSSIL HISTORY OF THE HAMAMELIDAE, VOL. 2, HIGHER HAMAMELIDAE, Clarendon Press, Oxford, U.K.); and most recently in its own family with hops (*Humulus*), Cannabaceae, or hemp family (Sytsma, K J, et al, 2002, AMERICAN JOURNAL OF BOTANY 89(9): 1531-1546). While the work of Small and Cronquist 1976 Supra, seemed to effectively confine the genus to a single species with 2 subspecies (*C. sativa* s., *C.* s. *indica*), each with two varieties (*C.* s. s. var. *sativa, C.* s. s. var. *spontanea*; *C.*s. i. var. *indica, C.* s. i. var. *Kafiristanica*) largely on the basis of chemotaxonomy and interfertility of all forms, more recent work (Sytsma et al. 2002 Supra), proposes a two-species concept, resurrecting the binomial *C. indica* Lam. Since Sytsma et al. (2002) provides no key for discriminating between the species, the dichotomous key of Small and Cronquist (1976), which accounts for all forms in nature, whether wild or domesticated, is preferred to classify the characteristics of the plants.

BRIEF SUMMARY OF THE INVENTION

The present invention relates to a new and distinct *Cannabis* cultivar designated 'ZLT'.

'ZLT' is a proprietary hybrid cultivar. The mother (not patented) is a mix of popular modern designer *Cannabis* genetics, a polyhybrid back cross of Motorbreath 15. Comprised of Gelato #41 crossed to Motorbreath #15 and then crossed back to Motorbreath #15. The mother plant is a proprietary phenotype and is not known to be patented or patent pending at this time. The father is the proprietary breeder stud 'Zuchi' (Pending U.S. Plant patent application Ser. No. 17/950,091). A single plant was selected from a population of 250 seedlings. The plants were grown and flowered indoors, in a tightly controlled environment, under mixed spectrum light conditions in order to see maximum genetic expression. The plants are able to withstand temperatures above 102 degrees Fahrenheit with 85 percent RH. The objective of 'ZLT's' creation was to unlock and identify new and unique smell and flavor profiles resulting from the enhanced terpene and flavonoid content.

Consumer demand continues to require new terpene and flavor profiles be brought to market, and in tandem, commercial operators need genetics that maximize wholesale cost while increasing profitability in the form of lower production costs, and increased harvest size. It is understood that it is not the cannabinoids themselves that drive and direct the effects of *Cannabis* but it is the other phytochemicals, specifically terpenes, flavonoids, esters and aldehydes that are responsible for the drastic difference in the perceived effects. Higher levels of Limonene are associated with an uplifting and euphoric effect, while myrcene is associated with effects that are described as calming and sleep inducing.

The inventor continues to actively create cultivars that suit their own needs and the needs of their clients. The particular cultivar described was discovered in an area where the inventors are intentionally cross-pollinating various cultivars using standard Mendelian breeding procedures well known to those of ordinary skill. This resulted in the seed stock from which the 'ZLT' plant was identified.

The inventor reproduces progenies asexually using stem cutting and cloning, as well as both nodal and meristem tissue culture. The plant continues to be asexually propagated at the inventor's greenhouses in Fallbrook, Calif.

The following are the most distinguishing and desirable chemical and physical characteristics when grown under normal conditions indoors under standard HID lighting. Chemical analysis was performed by the standard separation and isolation technique that is well known to those skilled in the art of analytical chemistry.

'ZLT' produces towering green, white and purple streaking resin-coated flowers. With very short internodal space and vigorous growth characteristics, this cultivar is able to produce very high yields for both flower and hash production. Yielding as much as 6% from fresh frozen material. Flower clusters have been observed at over 1-1.5' of uninterrupted colas. The claimed plant expressed a very unique and distinct rippled leaf and spiked flower structure and pattern that is more desirable to commercial cultivators due to ease of mechanical trimming and processing. The trichome heads are up to 10% larger and more tightly clustered as well. The selected plants express a shorter internodal length that allows for more flower sites within the same area, resulting in a larger overall yield of flower or resin. The most notable difference is the unique terpene and flavor profiles that are of spiced and freshly seared steak, gasoline, acetone, ocean mist and garlic. This unique combination of terpenes as described distinguishes ZLT from other varieties in its odor, flavor, and resulting medicinal or recreational effects.

'ZLT' is asexually propagated via removal of terminal colas from a mother plant. These cuttings are between 4-5" in length and are then inserted into rockwool cubes that are saturated with ph adjusted water with fertilizer. The plants are arranged in trays and covered with a clear dome to increase humidity and reduce light levels. The plants will sit covered for 5 days with a fresh air exchange every day under 24 hours of light. Starting on day 6 the plants will begin to root and require watering in the trays and the domes will be vented until the humidity matches that of the external environment. By day 10-12, the plants will be ready for transplant and will be inserted into 6×6×6" rockwool cubes that are conditioned at 5.8ph and 3.0ec. They will be moved into an area with 18 hours of light for 17-21 days until the root zone has fully developed. After the roots are seen to exit the bottom of the rockwool cubes, the plants will be moved into a room with only 12 hours of light to induce flowering. These plants will grow under 12 hours of light for 50-65 days and are then ready for harvest.

To harvest, the entire plant is cut at the base and then weighed and logged. The whole plant is then dried under controlled conditions that are cold and dark for 14-21 days before being carefully manicured and then allowed to rest for a further 14 days before final analysis.

Under careful analysis, asexually propagated 'ZLT's' unique flavor and terpene profile is stable and reproducible both indoors and in greenhouse, and while using different light fixtures and nutrient blends. The unique terpene and flavor profile described herein, distinguishes this cultivar from others currently available, including Applicant's co-pending plant patent applications 'TZT' (Ser. No. 17/950,089) and 'AFZ' (Ser. No. 17/950,086).

'ZLT' is a very hardy plant that is drought and mildew resistant while able to yield 450-750 grams/m2 in a sea-of-green style grow. The below numbers are the result of 1 selected phenotype from a population of only 10 seeds. A Sea of Green is way to describe growing many plants together to form a continuous canopy. As opposed to growing individual large plants to fill a space, this method groups smaller plants tightly together while maintaining a uniform appearance.

Dried flowers were obtained from the claimed plants. The below cannabinoid and terpene results were obtained by high-performance liquid and gas chromatography, otherwise known as HPLC and GCMS. The standard analytical methods for these procedures were utilized to obtain the following results.

Chemical Profile:
MAX CANNABINOIDS 30.5%
THC 0.5%
THCA 29.1%
CBG 0.2%
CBGA 0.7%
MAX TERPENES 2.24%
a-Pinene 0.04%
b-Pinene 0.06%
b-Myrcene 0.23%
Limonene 0.47%
Terpinolene 0.02%
Linalool 0.23%
b-Caryophyllene 0.60%
a-Humulene 0.15%
b-Eudesmol 0.07%

DETAILED BOTANICAL DESCRIPTION

Figure 1:
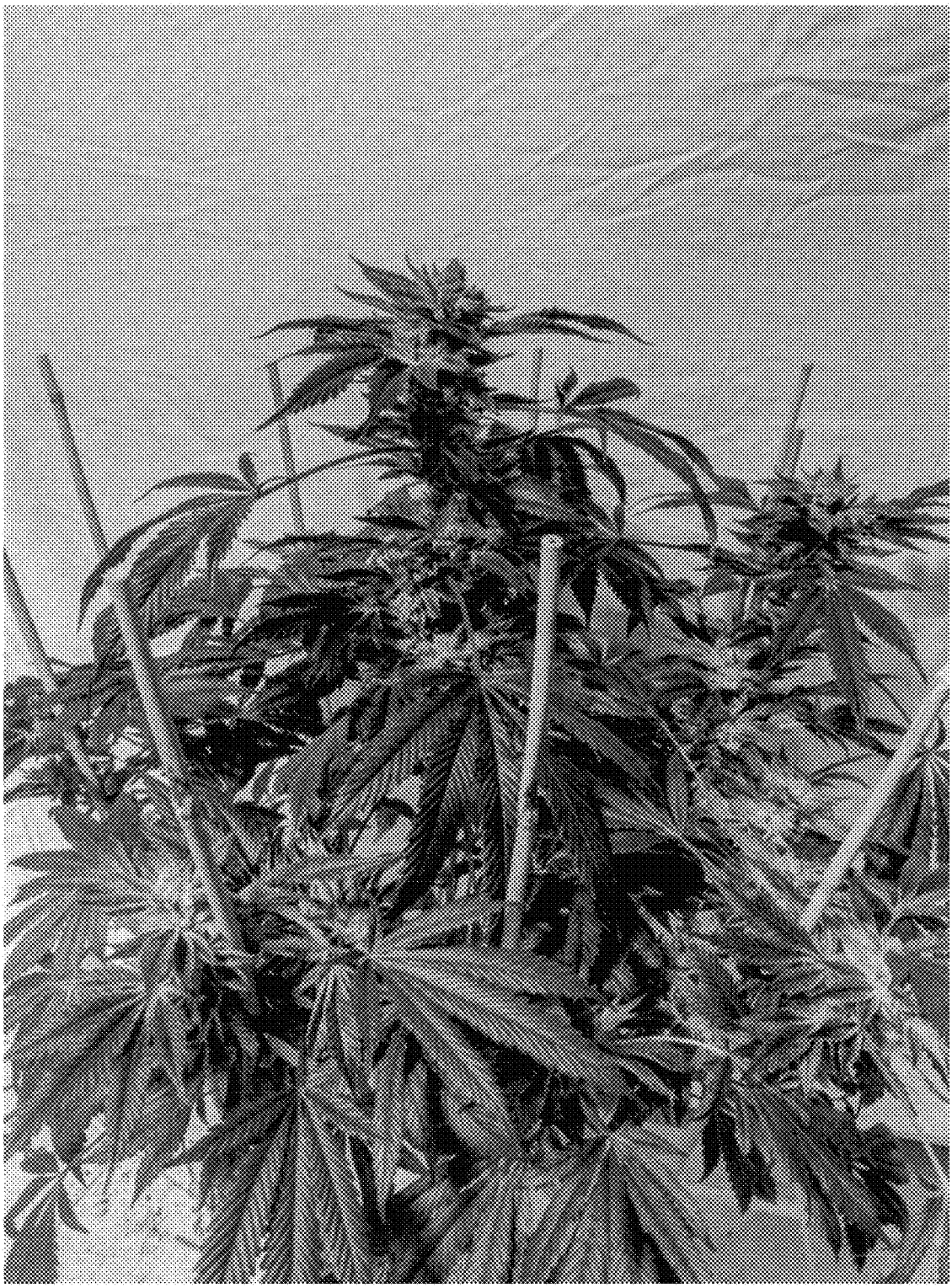
FIG. 1 is a view of the top of a flowering 'ZLT' plant.
Figure 2:
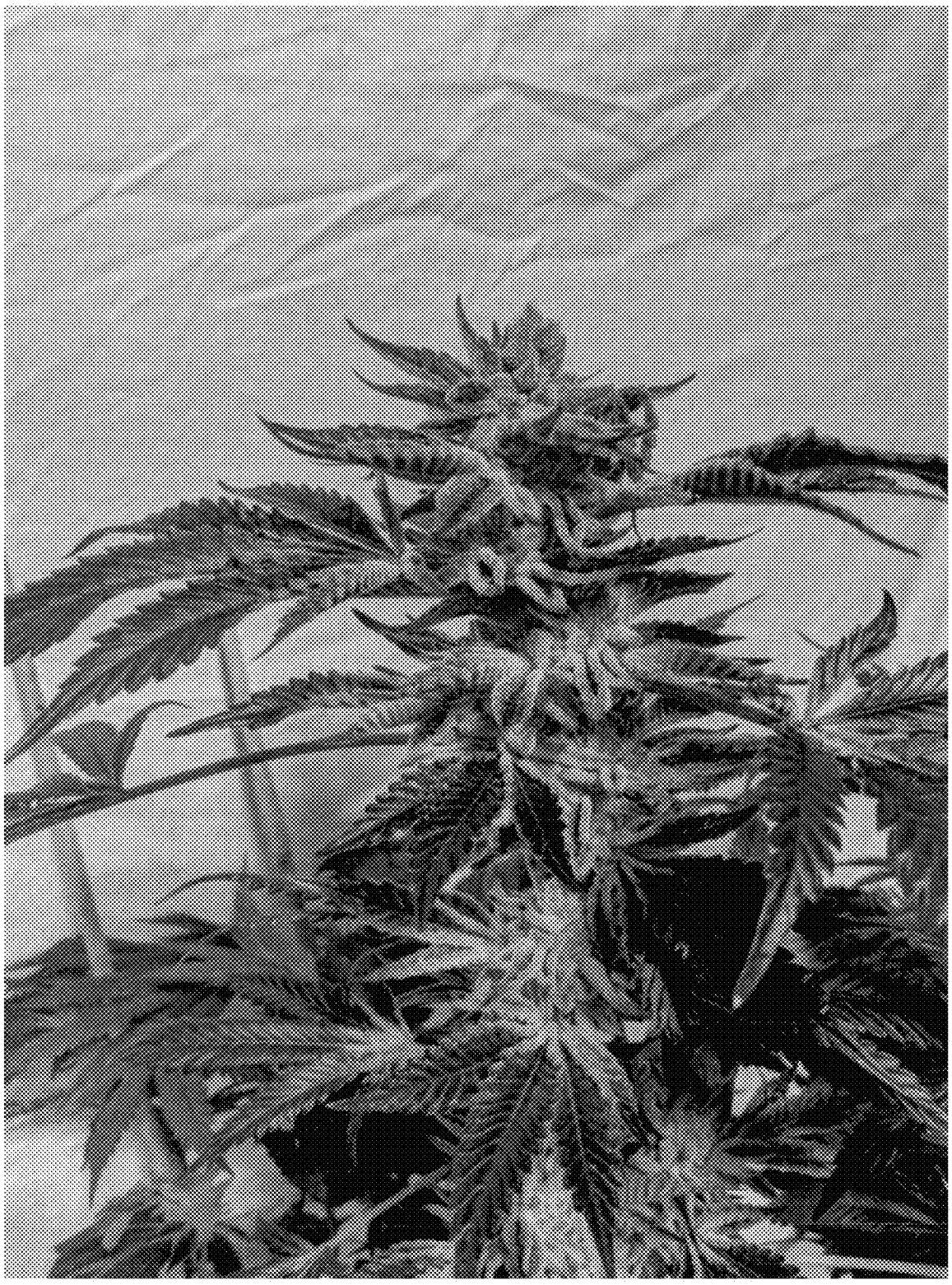
FIG. 2 is a close-up view of several 'ZLT' flower clusters on a growing 'ZLT' plant.
Figure 3:
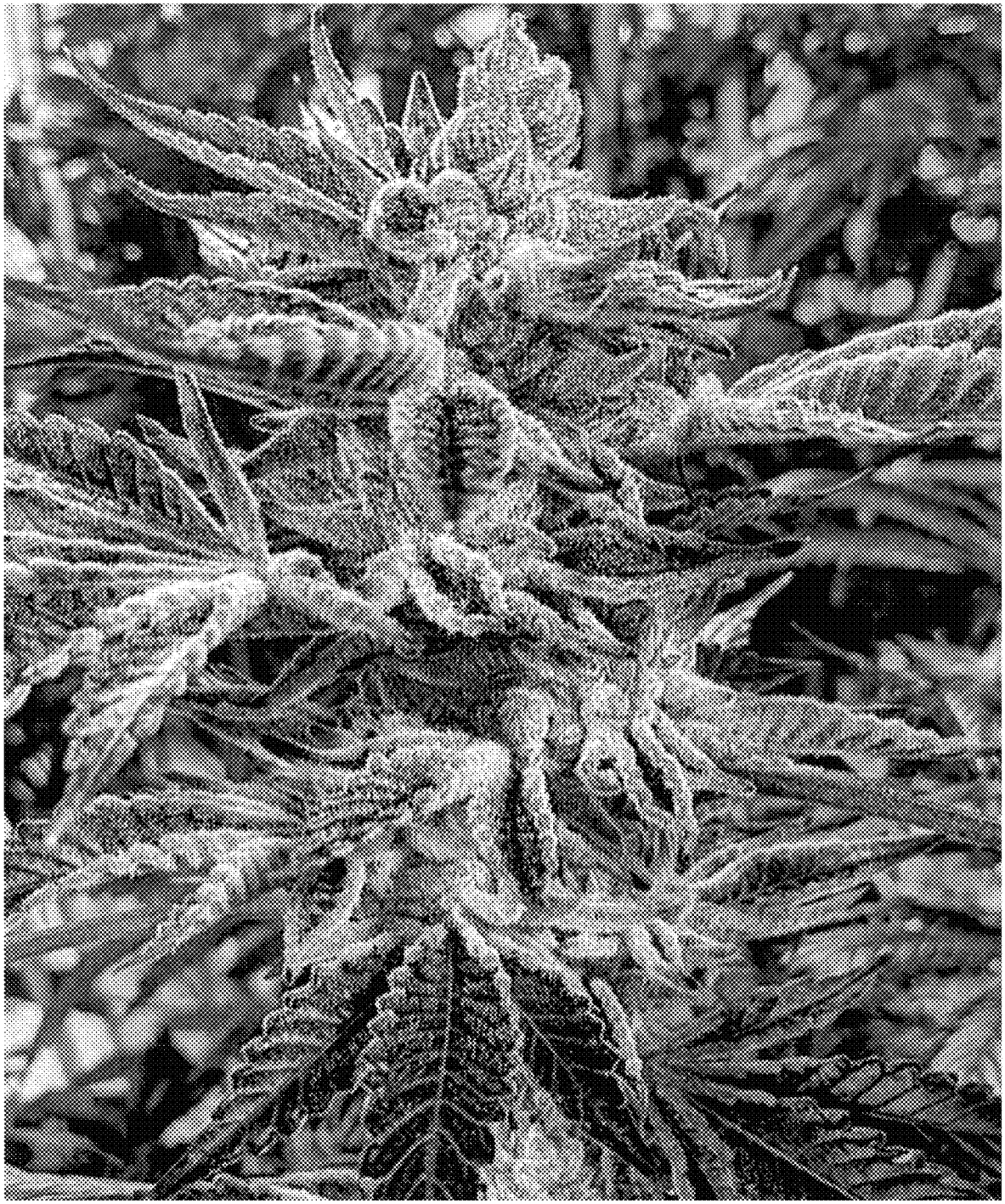
FIG. 3 is a close-up view of a 'ZLT' flower cluster on a growing 'ZLT' plant.
Figure 4:
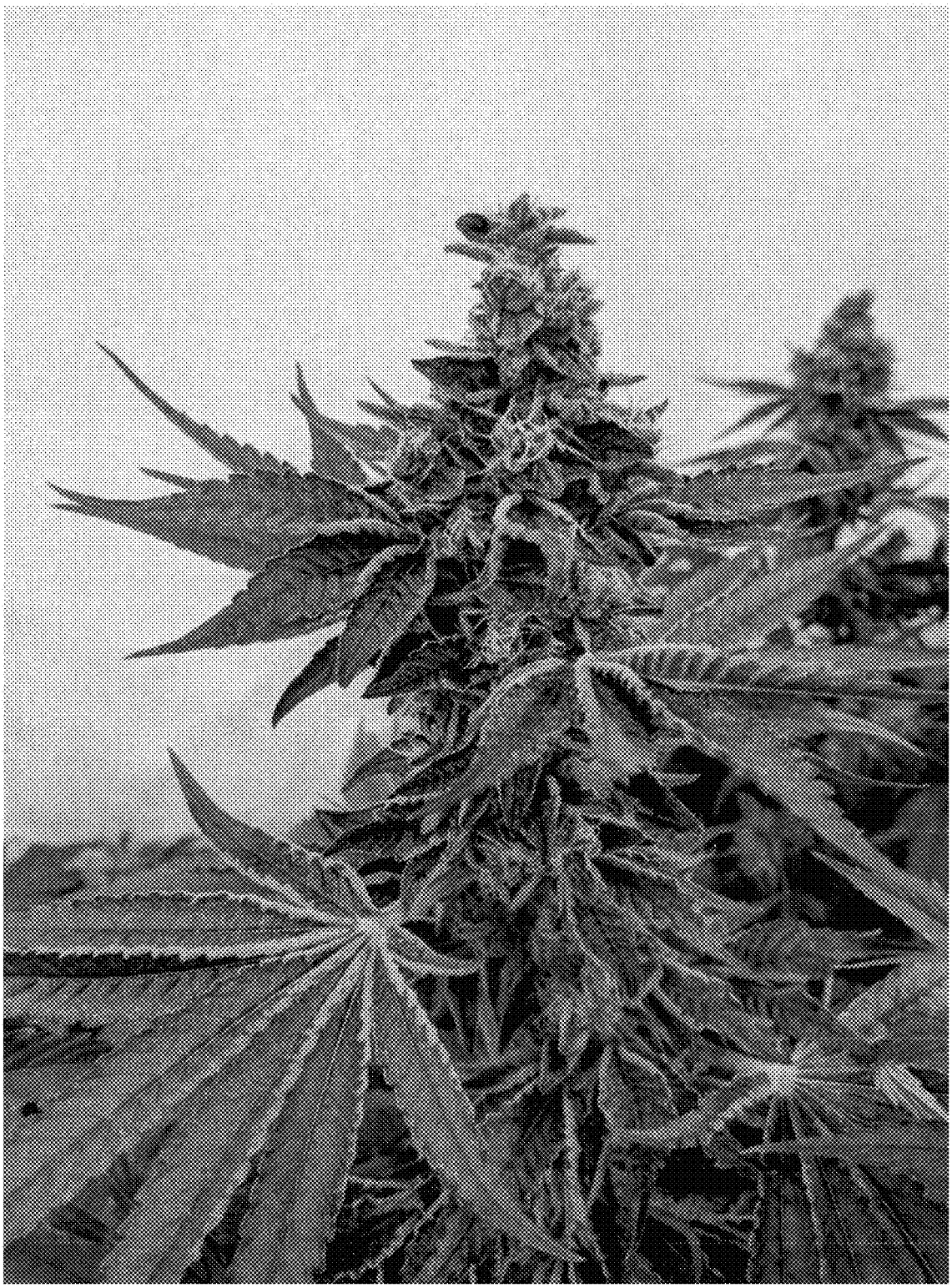
FIG. 4 is a close-up view of a 'ZLT' flower cluster on a growing 'ZLT' plant.
Figure 5:
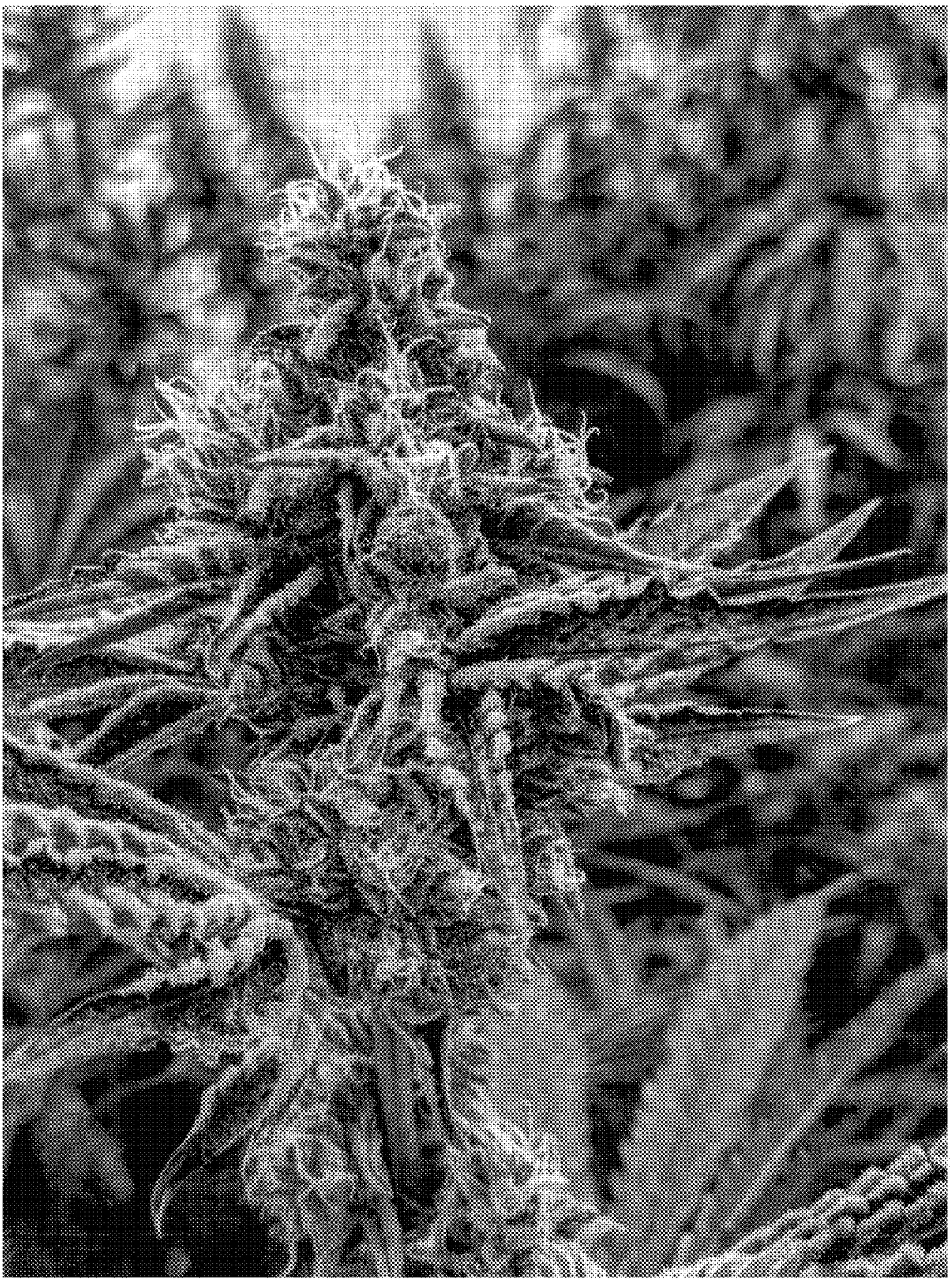
FIG. 5 is a close-up view of a 'ZLT' flower cluster on a growing 'ZLT' plant.

'ZLT' has not been observed under all possible environmental conditions, and the phenotype may vary significantly with variations in environment. The following observations, measurements, and comparisons describe this plant as grown at Mentone, Calif., when grown in the greenhouse, nursery or field, unless otherwise noted.

The color chart referenced is standard hexadecimal Web Pantone Color Chart well known to those of ordinary skill in Internet web site design.

DETAILED BOTANICAL DESCRIPTION

Type (life form and habit): Herbaceous tap-rooted annual.

*Seeds*.—The seeds are round/oval in shape with large zigzag striped patterns that cover the length of the seed. They are brown PMS 463 with strong marbling can weigh between 0.1-0.2 g each.

*Inflorescence*.—The flowers are bulbous at the base and emerge outward into sharp points. The % of male vs female plants was approximately 60% female and 40% males in the selection process. There was <1% hermaphrodite expression from seed and after taking clones, the hermaphroditic expression was not seen again. The flowers are arranged in a spiral pattern up the stem similar to Brussels sprouts with each flower being fully formed and not contributing to a homogeneous "cola" shape. Average number of flowers is 35-40 per plant with an average diameter of 3.5 cm. The flowers are dark green but look white PMS 350 and PMS 656 due to the heavy presence and density of the large trichomes on every square millimeter of the flower. The fragrance is that of spiced and freshly seared steak, gasoline, acetone and garlic, a very noxious and intense smell that can cause eye watering in some cases.

*Leaves*.—The fan leaves are large and stout. They can be 8-12" long and have a total width of 8-10" with some overlap between every leaflets. The trichomes are mostly capitate stalked and are wet and greasy to the touch, releasing a heavy aroma of freshly seared steak, gasoline, acetone, ocean mist and garlic. Leaflet shape is a long oval with ripples on all sides, they do not lie flat. An average number of leaflets is between 7-11 depending on the total plant size and health. The top of the leaf is dark green PMS 365 with the bottom being light green PMS 359.

*Petioles*.—Typically 2.2-4.5" long and 0.2-0.3" in diameter. The longer and older petioles will show anthocyanin production PMS 361 starting closer to the stem and moving out toward the leaf rachis. Trichomes are glandular with capitate stalked visible and bulbous trichomes and capitate-sessile all around. Petioles are dark green PMS 353 C with purple anthocyanin streaking PMS 260.

*Stems*.—The stem shape is a large oval that has a zig-zag pattern as it grows. Each node will begin to grow in the opposite direction of the previous node at the same angle of growth. The stem color is green, PMS 356. The stem is round and can reach a diameter of 1.25-1.5" when grown with a shallow groove depth and thick pith presence (full stems). There are no visible trichomes growing on the stem.

*Bract*.—The bract is dark green PMS 364 and 0.15" in diameter and 0.25" in length with 2 stigmas emerging from the center. They are absolutely covered with capitate-stalked trichomes and also house bulbous and capitate-sessile trichomes throughout.

*Bracteoles*.—Usually between 0.1-0.125" in length. They are slender spear-shaped and dark green PMS 578.

*Height*.—The average height can be modified depending on the volume of growing media and the irrigation frequency. In a 6×6×6 rockwool cube, being fed 1500-2000 ml per day a plant will average around 72" in height. The selected plant is grown in clusters with 9 plants per 16-24 ft2. An incredibly vigorous plant, clones will take between 6-10 days to show roots and will reach a height of 18-24" after only 17-21 days.

*Stipules*.—Found at each node and are usually between 0.2-0.25" in length. They are spear-shaped and accompanied by white pistils PMS 602 C regardless of the light cycle or season and are light green PMS 368 C.

Classification: Cultivars of *Cannabis sativa*. This cultivated line possesses intoxicating properties, and so the Subspecies *sativa* and its varieties (var. *sativa* and *spontanea*) are eliminated from consideration.

*Market use*.—The market use for this product is medical and recreational *Cannabis* flower as well as extracts and infused goods. They have been able to withstand temperature above 102 degrees Fahrenheit with 85 percent RH.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A new and distinct variety of *Cannabis* plant named 'ZLT', substantially as illustrated and described herein.

* * * * *